(12) United States Patent
Matsunami

(10) Patent No.: US 7,967,910 B2
(45) Date of Patent: Jun. 28, 2011

(54) FINE STRUCTURE BODY, PROCESS FOR PRODUCING THE SAME, AND RAMAN SPECTROSCOPIC METHOD AND APPARATUS

(75) Inventor: Yuki Matsunami, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 1203 days.

(21) Appl. No.: 11/601,822

(22) Filed: Nov. 20, 2006

(65) Prior Publication Data

US 2007/0118936 A1 May 24, 2007

(30) Foreign Application Priority Data

Nov. 18, 2005 (JP) .................................. 2005-334794

(51) Int. Cl.
*C30B 29/62* (2006.01)
(52) U.S. Cl. ...................... 117/4; 117/8; 117/9; 117/202
(58) Field of Classification Search .................. 117/4, 8, 117/9, 202
See application file for complete search history.

(56) References Cited

U.S. PATENT DOCUMENTS

| | | | |
|---|---|---|---|
| 7,288,419 B2 | 10/2007 | Naya | |
| 2005/0105085 A1 | 5/2005 | Naya | |
| 2006/0270229 A1* | 11/2006 | Corderman et al. | 438/689 |

FOREIGN PATENT DOCUMENTS

| | | |
|---|---|---|
| JP | 2005144569 A | 6/2005 |
| JP | 2005172569 A | 6/2005 |
| JP | 2005233637 A | 9/2005 |

OTHER PUBLICATIONS

J. L. Yao., et al, "A complementary study of surface-enhanced Raman scattering and metal nanorod arrays", Chem., vol. 72, No. 1, pp. 221-228, 2000.
A. Wei., et al, "Tunable Surface-enhanced Raman Scattering form Large Gold Nanoparticle Arrays", Chem. Phys.Chem., vol. 2, No. 12, pp. 743-745, 2001.
B. Nikoobakht and M. A. El-Sayed, "Surface-Enhanced Raman Scattering Studies on Aggregated Gold Nanorods", J. Phys.Chem. A vol. 107, No. 18, pp. 3372-3378, 2003.
X. Hu et al., "Fabrication, Characterization, and Application in SERS of Self-Assembled Polyelectrolyte-Gold Nanorod Multilayered Films", J. Phys. Chem. B, vol. 109, No. 41, pp. 19385-19389, 2005.
M. Suzuki., et al "Surface-Enhanced Nonresonance Raman Scattering of Rhodamine 6G Molecules Adsorbed on Gold Nanorod Films", Japan J. Appl. Phys., vol. 43, No. 4B, pp. L554-L556, 2004.
Japanese Office Action for Japanese Application No. 2005-334794 dated Dec. 28, 2010.

* cited by examiner

*Primary Examiner* — Robert M Kunemund
(74) *Attorney, Agent, or Firm* — Sughrue Mion, PLLC

(57) ABSTRACT

A fine structure body comprises: (i) a base body, and (ii) a plurality of metal nanorods, which have been distributed and located on a surface of the base body, a proportion X being equal to at least 15%, the proportion X being calculated with the formula:

$$X=(A-B)/C \times 100 [\%]$$

wherein A represents the sum total of the projected areas of all of the metal nanorods, B represents the sum total of the projected areas of certain metal nanorods, each of which is located as an isolated metal nanorod at a spacing larger than 10 nm from the closest metal nanorod, and C represents the entire projected area of the fine structure body, including regions free from the metal nanorods.

12 Claims, 2 Drawing Sheets

250nm

FINE STRUCTURE BODY, PROCESS FOR PRODUCING THE SAME, AND RAMAN SPECTROSCOPIC METHOD AND APPARATUS

BACKGROUND OF THE INVENTION

1. Field of the Invention

This invention relates to a fine structure body adapted to utilization for Raman spectroscopy. This invention also relates to a process for producing the fine structure body. This invention further relates to a Raman spectroscopic method and apparatus utilizing the fine structure body.

2. Description of the Related Art

Raman spectroscopy is a technique, wherein scattered light, which is obtained from irradiation of light having a single wavelength to a sample substance, is separated into spectral components of the scattered light, wherein a spectrum (hereinbelow referred to as the Raman spectrum) is thereby obtained, and wherein light (hereinbelow referred to as the Raman scattered light) having wavelengths different from the wavelength of the incident light is detected in accordance with the Raman spectrum. The Raman scattered light has a markedly low intensity. Therefore, ordinarily, it is not always possible to detect the Raman scattered light. However, it has been reported that, in cases where a sample substance is adsorbed onto a metal surface, and light is irradiated to the sample substance, the intensity of the Raman scattered light is capable of being enhanced by a factor of approximately 1E+04 to approximately 1E+06. Particularly, it has been known that, with a structure, in which fine metal particles of a nano order have been distributed and located on a surface for adsorption of a sample substance, the Raman scattered light is capable of being enhanced markedly. (Reference may be made to, for example, "A complementary study of surface-enhanced Raman scattering and metal nanorod arrays", J. L. Yao et al., Pure Appl. Chem., Vol. 72, No. 1, pp. 221-228, 2000.) It has been theorized that the enhancement of the Raman scattered light arises due to localized surface plasmon resonance. Specifically, it has been presumed that free electrons within the fine metal particles undergo resonance with an electric field of light and vibrate, a strong electric field thus occurs in the vicinity of the fine metal particles, and the Raman scattered light is enhanced by the effects of the strong electric field occurring in the vicinity of the fine metal particles.

With a process disclosed in, for example, "A complementary study of surface-enhanced Raman scattering and metal nanorod arrays", J. L. Yao et al., Pure Appl. Chem., Vol. 72, No. 1, pp. 221-228, 2000, an alumina layer is formed with anodic oxidation processing performed on aluminum, a metal is filled in fine holes, which are formed naturally in a surface layer of the thus formed alumina layer during the anodic oxidation processing, and a device having a structure, in which fine metal particles have been distributed and located, is thereby produced. Specifically, with the disclosed process, after the metal has been filled in the fine holes, a top region of the alumina layer is removed with etching processing, and head regions of the fine metal particles are thus protruded, such that the Raman scattered light may be enhanced by a strong electric field occurring at pointed ends of the head regions of the fine metal particles. With a process disclosed in, for example, U.S. Patent Application Publication No. 20050105085, an alumina layer is formed with anodic oxidation processing performed on aluminum, a metal is filled in fine holes, which are formed naturally in a surface layer of the thus formed alumina layer during the anodic oxidation processing, electroforming is continued even after the filling of the metal into the fine holes has been completed, and a device having a structure, in which spherical gold nanoparticles have been distributed and located, is thereby produced.

However, with each of the disclosed processes described above, the problems are encountered in that the number of processing steps is not capable of being kept small. Also, with each of the disclosed processes described above, the problems are encountered in that, in order for regularity of the fine holes formed by the anodic oxidation processing to be enhanced, it is necessary for Cr to be added. The addition of Cr is not appropriate from the view point of environmental protection. Further, with each of the disclosed processes described above, the problems are encountered in that, since precise condition setting is required for the production of the device, it is not always possible to produce the device with a high reproducibility.

With a process disclosed in, for example, "Tunable Surface-Enhanced Raman Scattering from Large Gold Nanoparticle Arrays", A. Wei et al., Chem. Phys. Chem., Vol. 2, No. 12, pp. 743-745, 2001, spherical gold nanoparticles are fixed to a surface of a base plate, and a device having a structure, in which the fine metal particles have been distributed and located, is thereby produced.

In cases where measurement for Raman scattering spectral analysis is to be made, a laser beam having a wavelength falling within a near infrared wavelength region (700 nm to 900 nm) is often utilized as the irradiation light. In such cases, in order for a high degree of the enhancement to be obtained, it is necessary that a surface plasmon absorption band of the gold nanoparticles be matched with the near infrared wavelength region. However, in cases where the spherical gold nanoparticles are utilized, it is necessary for the size of each of the gold nanoparticles to be set to be large, and the quantity of gold used becomes large. Therefore, in such cases, the cost is not capable of being kept low. Also, in the cases of the spherical particles, the area of the region, in which the adjacent particles are closest to each other, is small, and therefore a high degree of the enhancement is not capable of being obtained.

In, for example, "Surface-Enhanced Raman Scattering Studies on Aggregated Gold Nanorods", B. Nikoobakht and M. A. El-Sayed, J. Phys. Chem. A, Vol. 107, No. 18, pp. 3372-3378, 2003, the matter concerning Raman spectral analysis utilizing gold nanorods is reported. A process disclosed in the literature described above utilizes a two-stage technique, in which the gold nanorods are fixed to silica particles, and in which the gold nanorods having been fixed to the silica particles are thereafter fixed to a surface of a base plate. Also, in the literature described above, a report is made with respect to only the analysis of a surface-active agent, which has been adsorbed to surfaces of the gold nanorods at the time of synthesis of the gold nanorods, and nothing is reported with respect to the surface enhancement by the gold nanorods.

With a process disclosed in, for example, "Fabrication, Characterization, and Application in SERS of Self-Assembled Polyelectrolyte-Gold Nanorod Multilayered Films", X. Hu et al., J. Phys. Chem. B, Vol. 109, No. 41, pp. 19385-19389, 2005, metal nanorods are fixed by electrostatic attraction to a surface of a glass base plate by use of an alternating adsorption technique, and a device having a structure, in which the metal nanorods have been distributed and located, is thereby produced.

However, with the alternating adsorption technique, the metal nanorods are not capable of being fixed at a high density. Also, with the alternating adsorption technique, the distance between the metal nanorods and the orientation of the metal nanorods are not capable of being controlled. Therefore, it is not always possible to achieve sufficient enhancement of the intensity of the Raman scattered light and reproducible production of the device.

With a process disclosed in, for example, "Surface-Enhanced Non resonance Raman Scattering of Rhodamine 6G Molecules Adsorbed on Gold Nanorod Films", M. Suzuki et al., Japan. J. Appl. Phys., Vol. 43, No. 4B, pp. L554-L556, 2004, gold nanorods are aggregated at a water phase-oil phase interface, the gold nanorods having been aggregated is then transferred to a surface of a base plate, and a device having a structure, in which the metal nanorods have been distributed and located, is thereby produced.

However, with the technique, in which the gold nanorods are aggregated at the water phase-oil phase interface, the spacing between the gold nanorods is not capable of being controlled, and the gold nanorods are not capable of being distributed and located without defects on the surface of the base plate. Therefore, it is not always possible to achieve sufficient enhancement of the intensity of the Raman scattered light and reproducible production of the device. Also, the technique described above, in which an organic solvent is utilized, is not appropriate from the view point of environmental protection. Further, in, for example, "Surface-Enhanced Non resonance Raman Scattering of Rhodamine 6G Molecules Adsorbed on Gold Nanorod Films", M. Suzuki et al., Japan. J. Appl. Phys., Vol. 43, No. 4B, pp. L554-L556, 2004, nothing is mentioned with respect to a technique for adjusting the inter-particle distance between the gold nanorods, which inter-particle distance has a large effect on the degree of the enhancement, and a covering rate on the surface of the base plate, which covering rate has a large effect on the degree of the enhancement, and with respect to an optimum value of the inter-particle distance and an optimum value of the covering rate.

SUMMARY OF THE INVENTION

The primary object of the present invention is to provide a fine structure body, which is provided with a function of enhancing Raman scattered light, and which has high performance and high quality.

Another object of the present invention is to provide a process for easily and reliably producing a fine structure body, which is provided with a function of enhancing Raman scattered light, and which has high performance and high quality.

A further object of the present invention is to provide a Raman spectroscopic method, in which the fine structure body is employed.

A still further object of the present invention is to provide an apparatus for carrying out the Raman spectroscopic method.

The present invention provides a fine structure body, comprising:
  i) a base body, and
  ii) a plurality of metal nanorods, which have been distributed and located on a surface of the base body, and each of which has a size capable of inducing localized surface plasmon resonance.

The term "metal nanorod" as used herein means the rod-shaped metal nanoparticle having a minor axis length and a major axis length, which are different from each other.

Such that a high sensitivity analysis may be made, and such that a reproducible analysis may be made, the fine structure body in accordance with the present invention should preferably be designed such that a proportion of the metal nanorods located in a region, in which a distance between the metal nanorods adjacent to each other is equal to at most 10 nm, with respect to the region, in which all of the metal nanorods are located, is equal to at least 15%. Specifically, the fine structure body in accordance with the present invention should preferably be designed such that, in cases where the fine structure body is projected and observed (e.g., with a TEM), a proportion X is equal to at least 15%, the pro portion x being calculated with the formula:

$$X=(A-B)/C \times 100[\%]$$

wherein A represents the sum total of the projected areas of all of the metal nanorods, B represents the sum total of the projected areas of certain metal nanorods, each of which is located as an isolated metal nanorod at a spacing larger than 10 nm from the closest metal nanorod, and C represents the entire projected area of the fine structure body, including regions free from the metal nanorods.

The proportion X should preferably be equal to at least 50%, and should more preferably be equal to at least 70%.

It has been known that, at the region of the space between the metal nanorods adjacent to each other, an electric field stronger than the electric field occurring at the other regions arises. Therefore, in cases where at least one kind of spacing selected from the group consisting of the spacing between minor axis head regions of the metal nanorods adjacent to each other, the spacing between major axis side faces of the metal nanorods adjacent to each other, and the spacing between the minor axis head region of each of the metal nanorods and the major axis side face of the adjacent metal nanorod is set to be at most 10 nm, a large effect of enhancing the Raman scattered light is capable of being obtained. Accordingly, the fine structure body in accordance with the present invention should preferably be modified such that the fine structure body contains at least one region, in which at least one kind of spacing selected from the group consisting of the spacing between minor axis head regions of the metal nanorods adjacent to each other, the spacing between major axis side faces of the metal nanorods adjacent to each other, and the spacing between the minor axis head region of each of the metal nanorods and the major axis side face of the adjacent metal nanorod is equal to at most 10 nm.

Also, the fine structure body in accordance with the present invention should preferably be modified such that a minor axis length of each of the metal nanorods falls within the range of 3 nm to 50 nm. The minor axis length of each of the metal nanorods should more preferably fall within the range of 5 nm to 25 nm. Further, the fine structure body in accordance with the present invention should preferably be modified such that a major axis length of each of the metal nanorods falls within the range of 25 nm to 1,000 nm. The major axis length of each of the metal nanorods should more preferably fall within the range of 30 nm to 300 nm. Furthermore, the fine structure body in accordance with the present invention should preferably be modified such that an aspect ratio of each of the metal nanorods, which aspect ratio is defined by a value of major axis length/minor axis length of each of the metal nanorods, falls within the range of more than 1 to 100, inclusive. The aspect ratio of each of the metal nanorods should more preferably fall within the range of 2 to 20. It is sufficient for the shape of each of the metal nanorods to be of a rod-shaped anisotropic particle. For example, the shape of each of the metal nanorods may be a circular cylinder-like shape, a quadrangular prism-like shape, a triangular prism-like shape, a hexagonal prism-like shape, a dog bone-like shape, or the like.

Also, the fine structure body in accordance with the present invention should preferably be modified such that the metal nanorods are constituted of a material containing at least one kind of substance selected from the group consisting of gold, silver, aluminum, and copper.

The base body constituting the fine structure body in accordance with the present invention may be constituted of a Raman scattering-inactive material, such as glass, quartz, or a metal plate. Alternatively, the base body constituting the fine structure body in accordance with the present invention may be constituted of a Raman scattering-active material, such as silicon or a polyethylene, which has the characteristics such that a signal derived from the base plate may not adversely affect the detection of the substance to be analyzed. As the base body, to which gold nanorods are to be fixed, a base plate having hydrophilic characteristics, such as glass having a hydrophilic surface, is appropriate. As the base body, to which gold nanorods are to be fixed, it is also possible to employ a base plate constituted of a hydrophobic material, which base plate has been subjected to hydrophilic characteristics imparting processing. For modification of a fixing agent, such as dithiole, or for the enhancement of the surface plasmon resonance due to interference by the metal nanorods and a thin metal film, the base body may be coated with the thin metal film, such as a thin gold film. In cases where the glass surface is subjected to the hydrophilic characteristics imparting processing, the fixing rate of the metal nanorods is capable of being enhanced. Alternatively, the metal nanorods may be fixed to the base body by the utilization of a chemical bonding, an intermolecular force bonding, electrostatic force, or the like. As a fixing technique utilizing the chemical bonding, it is possible to employ a technique, in which the surface of the base plate is processed with, for example, a silane coupling agent having a thiol group, an amino group, or the like, at a terminal. As a fixing technique utilizing the electrostatic force, it is possible to employ a technique, in which the surface of the base plate is processed with, for example, a silane coupling agent having a carboxyl group, an amino group, or the like, at a terminal. The base body should preferably be constituted of a material, which is not dissolved in the sample substance, or a solvent contained in the sample substance, and the like.

The present invention also provides a process for producing a fine structure body comprising (i) a base body, and (ii) a plurality of metal nanorods, which have been distributed and located on a surface of the base body, and each of which has a size capable of inducing localized surface plasmon resonance, the process comprising the steps of:

a) developing the metal nanorods on a water surface, and b) scooping up the metal nanorods from the water surface onto the surface of the base body.

Specifically, for example, the fine structure body in accordance with the present invention may be produced with a process comprising the steps of: little by little adding a metal nanorod dispersion, which contains metal nanorods in a hydrophobic dispersion medium, onto a water surface, evaporating the dispersion medium, thereby forming a single particle-state film of the metal nanorods on the water surface, and thereafter scooping up the single particle-state film of the metal nanorods from the water surface onto a glass base body, which has been subjected to processing for fixation of the metal nanorods, such as washing or hydrophilic characteristics imparting processing. Alternatively, for example, the fine structure body in accordance with the present invention may be produced with a process, wherein a metal nanorod dispersion is coated onto a base plate surface by use of a coating technique, such as a spin coating technique or a bar coating technique.

As a technique for forming the single particle-state film of the metal nanorods on the water surface, it is possible to employ a technique, in which the metal nanorod dispersion is added little by little onto the surface of water contained in a vessel, such as a laboratory dish. It is also possible to employ an LE technique. Further, it is possible to employ one of various other techniques.

The distance between the metal nanorods adjacent to each other is capable of being adjusted by the adjustment of the concentration of the metal nanorod dispersion, which is added little by little onto the water surface, and the quantity of the metal nanorod dispersion added little by little onto the water surface. In the cases of the LB technique, the distance between the metal nanorods adjacent to each other is capable of being adjusted by the adjustment of the surface pressure.

Also, in the cases of the process, wherein the metal nanorod dispersion is coated onto the base plate surface by use of the coating technique, such as the spin coating technique or the bar coating technique, the distance between the metal nanorods adjacent to each other is capable of being adjusted by the adjustment of the concentration of the metal nanorod dispersion, the coating weight of the metal nanorod dispersion, the boiling temperature of the dispersion medium, the rotation speed, and the like.

The metal nanorods to be used for the production of the fine structure body in accordance with the present invention may be synthesized with a technique, such as a chemical reduction technique, an electrolytic technique, a photo-reduction technique, or a photochemical reduction technique. The metal nanorods to be used for the production of the fine structure body in accordance with the present invention may also be prepared with one of various other techniques. At the time of the synthesis of the metal nanorods, a surface-active agent may be added for regulation of the shape of the metal nanorods. By way of example, the synthesis of the metal nanorods may be performed by use of a quaternary ammonium salt, such as a cetyl trimethyl ammonium salt. The metal nanorods having the surfaces, to which the quaternary ammonium salt has been adsorbed, have the affinity for water. Therefore, the quaternary ammonium salt having been adsorbed to the surfaces of the metal nanorods may be replaced by a monomer dispersing agent, an oligomer dispersing agent, or a polymer dispersing agent, which dispersing agent has been dissolved in a hydrophobic solvent, such as chloroform, hexane, or toluene. In this manner, the metal nanorods may be imparted with the affinity for a hydrophobic dispersion medium. In such cases, the monomer dispersing agent, the oligomer dispersing agent, or the polymer dispersing agent may contain, for example, a functional group containing an S element, such as a thiol group or a dithiol group; a functional group containing an N element, such as an amine group or an amino group; or a functional group containing an O element, such as a carboxyl group or a hydroxyl group. The surfaces of the metal nanorods may be modified with one of other kinds of surface modifying agents. Also, at the time of the synthesis of the metal nanorods, an oil-soluble dispersing agent may be added.

As described above, the metal nanorods to be used for the production of the fine structure body in accordance with the present invention may be synthesized with the chemical reduction technique, the electrolytic technique, the photo-reduction technique, the photochemical reduction technique, or the like. Ordinarily, at the time of the synthesis of the metal nanorods, a surface-active agent is added for the regulation of the shape of the metal nanorods. Therefore, the surface-active agent has been adsorbed to the surfaces of the metal nanorods having been synthesized. Therefore, in order for a high enhancement degree of the fine structure body to be enhanced, after the metal nanorods have been fixed to the surface of the base body constituting the fine structure body, the fine structure body may be subjected to processing, such as sputtering processing, for removing organic substances from the surfaces of the metal nanorods.

The fine structure body in accordance with the present invention may be utilized as a bio chip, a sensor chip, and the like. In such cases, as the base body, to which the metal nanorods are fixed, a base body, whose front surface or rear surface has been subjected to marking, may be employed. As the marking technique, it is possible to utilize an ink jet technique, a screen printing technique, or one of various other techniques. Also, a base having a hole, or a base plate, such as glass, may be laminated with the base body, to which the metal nanorods have been fixed, and the bio chip or the sensor chip may thereby be formed.

Further, after the metal nanorods have been fixed to the base body, or after the surfaces of the metal nanorods having been fixed to the base body have been subjected to the post processing, such as the sputtering processing, a substance having a complementary effect with respect to a test body substance may be fixed to the surfaces of the metal nanorods. Examples of the complementary effects include an antigen-antibody reaction, a DNA hybridization, and a host-guest reaction. By way of example, the fixation of the substance having the complementary effect with respect to the test body substance may be performed with a technique for little by little adding with an ink jet technique, or the like.

The present invention further provides a Raman spectroscopic method, in which Raman spectroscopy is performed by the utilization of the fine structure body in accordance with the present invention. Specifically, the present invention further provides a Raman spectroscopic method, comprising the steps of:

a) obtaining a fine structure body comprising (i) a base body, and (ii) a plurality of metal nanorods, which have been distributed and located on a surface of the base body, and each of which has a size capable of inducing localized surface plasmon resonance, b) performing processing for causing a sample to be adsorbed to the surface of the fine structure body, on which surface the metal nanorods have been distributed and located, c) irradiating light to the surface of the fine structure body, to which surface the sample has been adsorbed, and d) separating scattered light of the irradiated light, which scattered light has been scattered from the surface of the fine structure body, into spectral components of the scattered light, whereby a spectrum of the scattered light is obtained.

In cases where the Raman spectroscopy is performed with the Raman spectroscopic method in accordance with the present invention, the Raman scattered light is sufficiently enhanced by the fine structure body, and therefore the Raman scattered light is capable of being detected with a high sensitivity.

The present invention still further provides a Raman spectroscopic apparatus, which utilizes the characteristics of the fine structure body in accordance with the present invention. Specifically, the present invention still further provides a Raman spectroscopic apparatus, comprising:

a) a fine structure body comprising (i) a base body, and (ii) a plurality of metal nanorods, which have been distributed and located on a surface of the base body, and each of which has a size capable of inducing localized surface plasmon resonance, b) light irradiating means for irradiating light to the surface of the fine structure body, on which surface the metal nanorods have been distributed and located, and c) spectroscopic means for separating scattered light of the light having been irradiated by the light irradiating means, which scattered light has been scattered from the surface of the fine structure body, into spectral components of the scattered light, and thereby obtaining a spectrum of the scattered light.

With the fine structure body in accordance with the present invention, in cases where the fine structure body is utilized for making the spectral analysis utilizing the surface-enhanced Raman scattering, the effects described below are capable of being obtained.

Specifically, with the fine structure body in accordance with the present invention, in which the metal nanorods have been fixed to the surface of the base body, the Raman spectral measurement is capable of being simplified.

Also, with the fine structure body in accordance with the present invention, in which the metal nanorods have been fixed to the surface of the base body, in cases where the fine structure body is utilized as an analysis device, the fine structure body is capable of being washed with an appropriate solvent and is thus capable of being used again for making a next analysis.

Further, in cases where the fine structure body in accordance with the present invention is utilized for making a Raman spectral analysis, in which a laser beam having a wavelength falling within the near infrared wavelength region (700 nm to 900 nm) is utilized as the exciting light, the strong surface plasmon resonance absorption derived from the major axis of each of the metal nanorods is capable of being excited, and therefore a high degree of enhancement is capable of being obtained.

Furthermore, with the fine structure body in accordance with the present invention, the metal nanorods have an area of a region yielding a high degree of enhancement (i.e., the region, in which the metal nanorods adjacent to each other is close to each other), which area is larger than the area of the region yielding a high degree of enhancement in the cases of spherical nanoparticles (i.e., the region, in which the spherical nanoparticles adjacent to each other is close to each other). Therefore, with the fine structure body in accordance with the present invention, a high-sensitivity enhancement device for Raman spectral analysis is capable of being furnished.

Also, with the fine structure body in accordance with the present invention, the metal nanorods have an electric field enhancing effect obtained in cases where the metal nanorods are located close to one another (the distance between pointed ends of adjacent particles <10 nm), which electric field enhancing effect is larger than the electric field enhancing effect of the spherical nanoparticles. Therefore, with the fine structure body in accordance with the present invention, the Raman spectral analysis is capable of being made with a high sensitivity even under non-resonance Raman conditions for the sample.

Further, with the fine structure body in accordance with the present invention, the spacing between adjacent metal nanorods and the orientation of each of the metal nanorods are capable of being regulated by the adjustment of a molecular length of the surface-active agent, which is utilized at the time of the synthesis of the metal nanorods, the quantity of the metal nanorod dispersion added little by little onto the water surface, the concentration of the metal nanorod dispersion, the surface pressure, or the like. Therefore, with the fine structure body in accordance with the present invention, a high-sensitivity enhancement device for Raman spectral analysis is capable of being furnished.

With the process for producing a fine structure body in accordance with the present invention, the effects described below are capable of being obtained for the production of a surface enhancement chip for Raman spectral analysis.

Specifically, with the process for producing a fine structure body in accordance with the present invention, the dispersion containing the metal nanorods in a hydrophobic dispersion medium may be added little by little onto the water surface, the single particle-state film may thereby be formed on the water surface, and the single particle-state film may then be transferred onto the surface of the base body. Alternatively, the metal nanorod dispersion may be coated on the surface of the base body, the coating layer of the metal nanorod dispersion may then be dried, and the fine structure body may thereby be produced. Therefore, with the process for producing a fine structure body in accordance with the present invention, the fine structure body is capable of being produced easily.

In cases where the fine structure body is produced by the utilization of the LB technique, the spin coating technique, or the like, the reproducibility and the uniformity of the production of the fine structure body are capable of being kept good.

Also, in cases where the fine structure body is produced by the utilization of the LB technique, the spin coating technique, or the like, the spacing between adjacent metal nanorods and the orientation of each of the metal nanorods are capable of being regulated. Therefore, the degree of enhancement is capable of being adjusted.

In cases where a comparison is made with respect to an identical surface plasmon resonance band, the quantity of the metal required for the metal nanorods is smaller than the quantity of the metal required for the spherical nanoparticles.

The present invention will hereinbelow be described in further detail with reference to the accompanying drawings.

DETAILED DESCRIPTION OF THE INVENTION

Figures 1A, 1B, 1C:
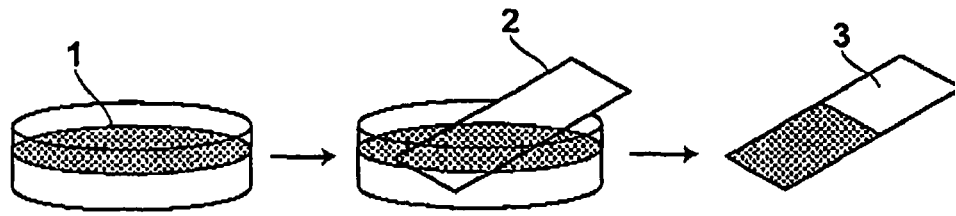
FIGS. 1A, 1B, and 1C are explanatory views showing an embodiment of the process for producing a fine structure body in accordance with the present invention.

An embodiment of the process for producing a fine structure body in accordance with the present invention will be described hereinbelow. The fine structure body in accordance with the present invention may be produced with one of various processes. In the embodiment of the process for producing a fine structure body in accordance with the present invention, a single particle-state film 1 of metal nanorods is formed on a surface of water contained in a glass laboratory dish. Also, the single particle-state film 1 of the metal nanorods is transferred from the water surface onto a glass base plate 2, which has been subjected to hydrophilic characteristics imparting processing. FIGS. 1A, 1B, and 1C are explanatory views showing an embodiment of the process for producing a fine structure body 3 in accordance with the present invention.

In cases where gold nanorods are employed as the metal nanorods; for example, the gold nanorods may be synthesized in a solution containing a cationic surface-active agent, such as cetyl trimethyl ammonium bromide. In such cases, one of various synthetic techniques may be employed. Examples of the synthetic techniques include a chemical reduction technique (as described in, for example, "Seed-Mediated Synthesis of Gold Nanorods: Role of the Size and Nature of the Seed", C. J. Murphy et al., Chem. Mater., Vol. 16, pp. 3633-3640, 2004), a photochemical reduction technique (as described in, for example, "Rapid Synthesis of Gold Nanorods by the Combination of Chemical Reduction and Photo irradiation Processes", Y. Niidome et al., Chem. Commun., pp. 2376-2377, 2003), and an electrochemical reduction technique (as described in, for example, U.S. Patent Application Publication No. 20050105085). The gold nanorods having the surfaces, to which the cationic surface-active agent has been adsorbed, have the affinity for water. Therefore, the cationic surface-active agent having been adsorbed to the surfaces of the gold nanorods may be replaced by a monomer dispersing agent, an oligomer dispersing agent, or a polymer dispersing agent, which dispersing agent has been dissolved in a hydrophobic solvent, such as chloroform, hexane, or toluene. In this manner, the gold nanorods may be imparted with the affinity for a hydrophobic dispersion medium. In such cases, the monomer dispersing agent, the oligomer dispersing agent, or the polymer dispersing agent may contain, for example, a functional group containing an S element, such as a thiol group or a dithiol group; a functional group containing an N element, such as an amine group or an amino group; or a functional group containing an O element, such as a carboxyl group or a hydroxyl group. The surfaces of the metal nanorods may be modified with one of other kinds of surface modifying agents. Also, at the time of the synthesis of the metal nanorods, an oil-soluble dispersing agent may be added.

The surfaces of the metal nanorods have been covered with an organic substance, such as the surface-active agent or a surface treatment agent, which have been adsorbed to the surfaces of the metal nanorods. The organic substance covering the surfaces of the metal nanorods also acts to regulate the closest distance between the metal nanorods adjacent to each other.

The metal nanorods having been obtained in the manner described above may be dispersed in a hydrophobic dispersion medium, such as chloroform or toluene. The thus obtained metal nanorod dispersion may be added little by little onto the surface of water contained in a laboratory dish, a trough of an LB apparatus, or the like, and the dispersion medium contained in the metal nanorod dispersion may then be removed by evaporation In the cases of the surface of water contained in the laboratory dish, which surface has a predetermined area, the quantity, with which the single particle-state thin metal nanorod film is capable of being formed on the water surface, may be adjusted by the adjustment of the concentration of the metal nanorod dispersion added little by little on to the water surface or the quantity of the metal nanorod dispersion added. In cases where the surface area of the water surface is capable of being adjusted as in the LB apparatus, the surface area of the water surface may be set to be small, the spacing between the metal nanorods adjacent to each other may thus be set to be small, and the single particle-state film may thereby be formed.

Thereafter, the single particle-state film of the metal nanorods having been formed on the water surface is transferred onto the base plate, which has been subjected to the hydrophilic characteristics imparting processing, or the like. In cases where an apparatus, in which the surface pressure of the water surface and the base plate drawing-up speed are capable of being kept at predetermined values, as in the cases of the LB apparatus, a more uniform single particle-state film of the metal nanorods is capable of being transferred onto the base plate. The base plate, which has been subjected to the hydrophilic characteristics imparting processing, is capable of being prepared with, for example, the processing, in which washing processing with a UV ozone cleaner or an alkaline washing liquid is performed on the glass base plate. The base body may be constituted of a Raman scattering-inactive material, such as glass, quartz, or a metal plate. Alternatively, the base body may be constituted of a Raman scattering-active material, such as silicon or a polyethylene, which has the characteristics such that a signal derived from the base plate may not adversely affect the detection of the substance to be analyzed. As the base body, to which gold nanorods are to be fixed, a base plate having hydrophilic characteristics, such as glass having a hydrophilic surface, is appropriate. As the base body, to which gold nanorods are to be fixed, it is also possible to employ a base plate constituted of a hydrophobic material, which base plate has been subjected to the hydrophilic characteristics imparting processing. In cases where the glass surface is subjected to the hydrophilic characteristics imparting processing, the fixing rate of the metal nanorods is capable of being enhanced. Alternatively, the metal nanorods may be fixed to the base body by the utilization of a chemical bonding, an intermolecular force bonding, electrostatic force, or the like. As a fixing technique utilizing the chemical bonding, it is possible to employ a technique, in which the surface of the base plate is processed with, for example, a silane coupling agent having a thiol group, an amino group, or the like, at a terminal. As a fixing technique utilizing the electrostatic force, it is possible to employ a technique, in which the surface of the base plate is processed with, for example, a silane coupling agent having a carboxyl group, an amino group, or the like, at a terminal. The base body should preferably be constituted of a material, which is not dissolved in the sample substance, or a solvent contained in the sample substance, and the like.

Figure 2:
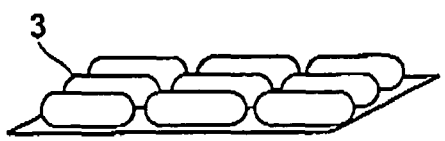
FIG. 2 is an explanatory view showing an embodiment of the fine structure body in accordance with the present invention.
Figure 3:
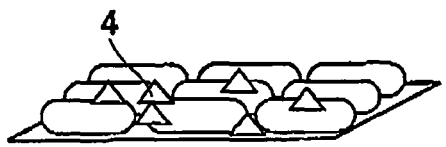
FIG. 3 is an explanatory view showing the fine structure body of FIG. 2 in a state in which a sample substance has been adsorbed to a surface of the fine structure body.

In the manner described above, the fine structure body 3 as illustrated in FIG. 2 is produced. FIG. 2 is an explanatory view showing an embodiment of the fine structure body in accordance with the present invention. In cases where the Raman spectral analysis is to be made by use of the fine structure body (the device) in accordance with the present invention, a liquid containing the sample substance in a solvent is added onto the fine structure body and dried, and the sample substance is thus adsorbed to the surface of the fine structure body. FIG. 3 is an explanatory view showing the fine structure body of FIG. 2 in a state in which a sample substance has been adsorbed to a surface of the fine structure body. In FIG. 3, the reference numeral 4 represents the sample substance having been adsorbed to the surface of the fine structure body. In the state, in which the sample substance has been adsorbed to the surface of the fine structure body, the laser beam for excitation is irradiated to the fine structure body.

The metal nanorods employed in the Raman spectroscopic method in accordance with the present invention should preferably have a shape as described below. Specifically, the minor axis length of each of the metal nanorods should preferably fall within the range of 3 nm to 50 nm. The minor axis length of each of the metal nanorods should more preferably fall within the range of 5 nm to 25 nm. Further, the major axis length of each of the metal nanorods should preferably fall within the range of 25 nm to 1,000 nm. The major axis length of each of the metal nanorods should more preferably fall within the range of 30 nm to 30 nm. Furthermore, the aspect ratio of each of the metal nanorods, which aspect ratio is defined by the value of major axis length/minor axis length of each of the metal nanorods, should preferably fall within the range of more than 1 to 100, inclusive. The aspect ratio of each of the metal nanorods should more preferably fall within the range of 2 to 20. It is sufficient for the shape of each of the metal nanorods to be of a rod-shaped anisotropic particle. For example, the shape of each of the metal nanorods may be a circular cylinder-like shape, a quadrangular prism-like shape, a triangular prism-like shape, a hexagonal prism-like shape, a dog bone-like shape, or the like. For example, the gold nanorods exhibit two surface plasmon absorption bands, i.e., a surface plasmon absorption band in the vicinity of a wavelength of 520 nm, which surface plasmon absorption band is derived from the minor axis of each of the gold nanorods, and a surface plasmon absorption band in the vicinity of a wavelength falling within the range of 600 nm to 1,500 nm, which surface plasmon absorption band is derived from the major axis of each of the gold nanorods. Therefore, with the Raman spectroscopic method in accordance with the present invention, in cases where the laser beam having a wavelength falling within the near infrared wavelength region (700 nm to 900 nm), preferably a wavelength of 785 nm, is irradiated to the fine structure body comprising the gold nanorods, it is possible to excite the surface plasmon resonance of the major axis of each of the gold nanorods, and a high SERS enhancement degree is capable of being obtained. However, it is necessary for the intensity of the laser beam irradiated to the fine structure body to be suppressed to a level such that the metal nanorods may not be deformed or fused.

It has been known that, at the region of the space between the metal nanorods adjacent to each other, an electric field stronger than the electric field occurring at the other regions arises. Therefore, in cases where at least one kind of spacing selected from the group consisting of the spacing between minor axis head regions of the metal nanorods adjacent to each other, the spacing between major axis side faces of the metal nanorods adjacent to each other, and the spacing between the minor axis head region of each of the metal nanorods and the major axis side face of the adjacent metal nanorod is set to be at most 10 nm, a large effect of enhancing the Raman scattered light is capable of being obtained. Besides the process for producing the fine structure body by use of the metal nanorods having been prepared, in order for the fine structure body to be produced with a high reproducibility, the fine structure body in accordance with the present invention may be produced with a process, in which rod-shaped recess areas and rod-shaped protruding areas are formed on a surface of a resin or glass by use of a nanoimprinting technique, and thereafter vacuum evaporation processing with gold, silver, aluminum, or the like, is performed.

Such that the analysis may be made with a high sensitivity or a high reproducibility, the proportion of the sum total of the projected areas of the metal nanorods, which are located at a spacing of at most 10 nm from one another, to the entire projected area of the fine structure body, including regions free from the metal nanorods, should preferably be at least 15%.

Also, the metal nanorods should preferably be constituted of a material containing at least one kind of substance selected from the group consisting of gold, silver, aluminum, and copper.

EXAMPLES

The present invention will further be illustrated by the following non-limitative examples.

Example 1

Production of the Fine Structure Body

Figure 4:
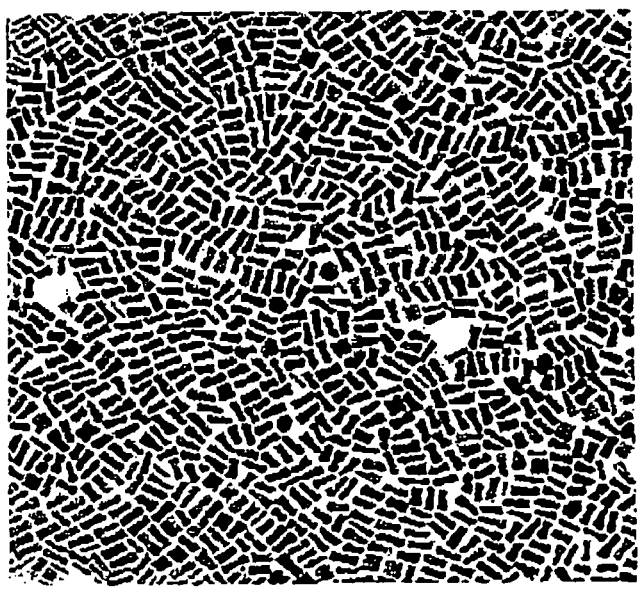
FIG. 4 is a diagram showing a TEM image of a fine structure body comprising gold nanorods (a device A)
Figure 5:
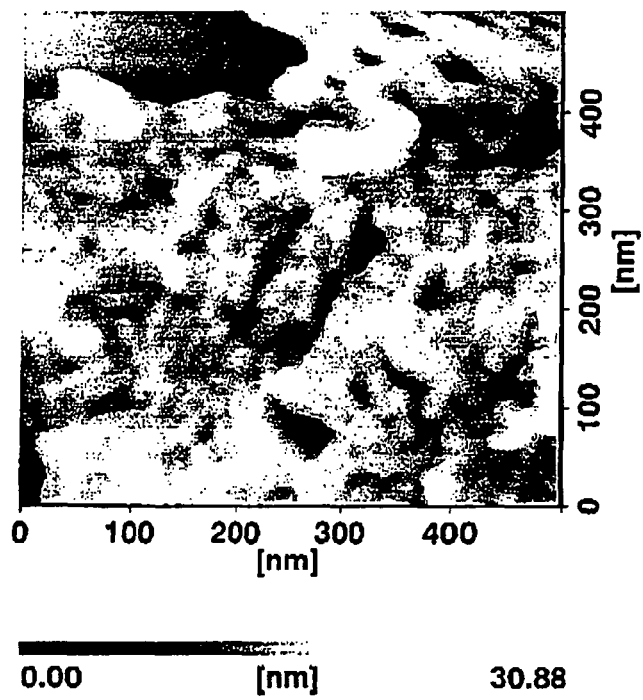
FIG. 5 is a diagram showing an AFM image of the fine structure body comprising the gold nanorods (the device A)

The device (acting as the fine structure body) 3, which comprised the base plate 2 and the gold nanorod thin film 1 having been fixed to the base plate 2, was produced in accordance with the procedure illustrated in FIGS. 1A, 1B, and 1C. Specifically, firstly, deionized water was introduced into a glass laboratory dish having an inside diameter of 7.0 cm. Thereafter, 30 μl of a gold nanorod dispersion, which contained gold nanorods having a minor axis length of approximately 13 nm and a major axis length of approximately 45 nm in chloroform, and which had been adjusted at a gold solid concentration of 1 wt %, was added little by little onto the surface of the deionized water. From the result of a calculation made in accordance with the size of the gold nanorods, it was found that approximately $6.6 \times 10^{12}$ pieces of the gold nanorods would be capable of being located so as to stand side by side on the surface of the deionized water contained in the glass laboratory dish having the inside diameter of 7.0 cm. Therefore, the quantity of the gold nanorod dispersion added little by little onto the water surface was set such that the number of the gold nanorods contained in the gold nanorod dispersion added might be equivalent to the number capable of forming the single particle-state film of the gold nanorods. After chloroform had been removed by evaporation, it was found that a film, which was tinted with blue in the cases of transmission and had metallic luster in the cases of reflection, had been formed on the water surface. After the gold nanorod thin film 1 had been washed with an alkaline washing liquid, a quartz glass base plate 2, which had previously been subjected to hydrophilic characteristics imparting processing with a UV ozone cleaner, was obliquely inserted into deionized water and was then slowly drown up. The gold nanorod thin film 1 was thus capable of being transferred without deformation on to the quartz glass base plate 2. Thereafter, the gold nanorod thin film 1 was subjected to natural drying. In this manner, the device 3, which comprised the base plate 2 and the gold nanorod thin film 1 having been fixed to the base plate 2, was obtained. (The thus obtained device 3 will hereinbelow be referred to as a device A.) Also, as a sample for comparison, a device (a device B), in which the density of the gold nanorods was reduced to 14% by the setting of the quantity of the gold nanorod dispersion added little by little onto the water surface at as small as 6 μl, was produced in the same manner as the procedure described above. Further, for comparison, a device (a device C) comprising a single particle-state film of spherical gold nanoparticles having a particle diameter of approximately 10 nm was produced in the same manner as the procedure described above. FIG. 4 is a diagram showing a transmission type electron beam microscope (TEM) image of the device A. FIG. 5 is a diagram showing an interatomic force microscope (AFM) image of the device A. From the TEM image illustrated in FIG. 4 and the AFM image illustrated in FIG. 5, it was confirmed that the gold nanorods having been fixed onto the base plate had formed the single particle-state film and that the particle spacing between the gold nanorods adjacent to each other was equal to approximately 4 nm.

Example 2

Raman Scattering Measurement

As for each of the device A, the device B, and the device C having been produced in Example 1, the Raman scattering measurement was made in the manner described below. Specifically, as the substance to be analyzed, a 260 μmol/l ethanol solution of Rhodamine 6G was used. As for each of the device A, the device B, and the device C, 10 μl of the aforesaid ethanol solution was added little by little onto the fine structure body surface having an area of $1.4 \times 1.7$ cm$^2$. After ethanol was removed by evaporation, a Raman spectrum was measured. As the Raman measuring apparatus, LabRAM HR-800 (supplied by Horiba Co.) was used. The exciting laser beam wavelength was 785 nm, and the laser power was 30 mW. Since Rhodamine 6G did not exhibit absorption in the near infrared wavelength region, the effect of the resonance Raman scattering did not occur.

Figure 6:
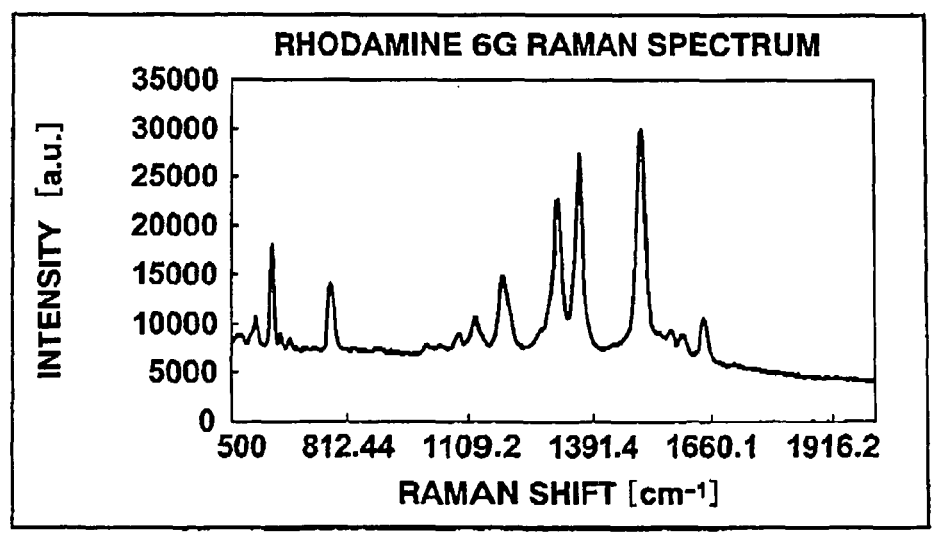
FIG. 6 is a graph showing a Raman scattering spectrum obtained with the device A, to which Rhodamine 6G has been adsorbed.

FIG. 6 is a graph showing a Raman scattering spectrum obtained with the device A, to which Rhodamine 6G has been adsorbed. The device A in accordance with the present invention, to which Rhodamine 6G had been adsorbed, exhibited the Raman scattering spectrum, whose peak band coincided with the peak band in the spectrum of the Rhodamine 6G particles. Also, from the device A alone, the device B alone, and the device C alone, only the scattering derived from the glass base plate was observed. From the foregoing, it was confirmed that, by the utilization of the device to which the gold nanorods had been fixed, the Raman scattering intensity of Rhodamine 6G was enhanced. Table 1 shown below indicates area occupying rates of gold and Raman scattering intensities (1505 cm$^{-1}$) of the device A, the device B, and the device C, to which Rhodamine 6G had been adsorbed. As shown in Table 1, as for the device A, in which the area occupying rate of gold was 70%, the 1505 cm$^{-1}$ corrected intensity derived from Rhodamine 6G was as high as 24810 a.u., and a high sensitivity was obtained. As for the device B, in which the density of the gold nanorods was low, and in which the area occupying rate of gold was 14%, the detection intensity was as low as 4526 a.u. and was insufficient for a high sensitivity analysis. From the foregoing, it was found that the inter-particle distance between the gold nanorods adjacent to each other should preferably be at most 10 nm, and that the area occupying rate of gold should preferably be at least 15%. Also, as shown in Table 1, as for the device C, which comprised the thin film of the spherical gold nanoparticles having a particle diameter of approximately 10 nm, the 1505 cm$^-$corrected intensity derived from Rhodamine 6G was as low as 216 a.u., and the enhancement effect was thus small. From the foregoing, it was confirmed that, in cases where a comparison was made with respect to an identical area occupying rate of gold, the rod-shaped particles had an enhancement effect larger than the enhancement effect of the spherical nanoparticles. The term "area occupying rate" as used herein means the value calculated with the division of the gold area by the base plate area, as viewed from above. In this case, since the gold nanorod particles, each of which is located as an isolated gold nanorod particle at a spacing larger than 10 nm from the closest gold nanorod, are not present, the area occupying rate corresponds to the proportion X as defined above.

TABLE 1

| Device | Shape | Area occupying rate of gold (%) | Rhodamine 6G 1505 cm$^{-1}$ Raman scattering intensity (a.u.) |
|---|---|---|---|
| A | Rod | 70 | 24810 |
| B | Rod | 14 | 4526 |
| C | Sphere | 70 | 216 |

INDUSTRIAL APPLICABILITY

As clear from the foregoing, with the fine structure body in accordance with the present invention, in which the metal nanorods have been located close to one another and fixed to the base body, a high sensitivity and simple Raman scattering spectral analysis capable of being utilized for substance measurement is capable of being made in a wide variety of industrial fields.

What is claimed is:

1. A fine structure body, comprising:
  i) a base body, and
  ii) a plurality of metal nanorods, which have been distributed and located on a surface of the base body,
  a proportion X being equal to at least 15%, the proportion X being calculated with the formula:

$X=(A-B)/C\times 100[\%]$ wherein A represents the sum total of the projected areas of all of the metal nanorods, B represents the sum total of the projected areas of certain metal nanorods, each of which is located as an isolated metal nanorod at a spacing larger than 10 nm from the closest metal nanorod, and C represents the entire projected area of the fine structure body, including regions free from the metal nanorods and
  wherein the metal nanorods are provided such that the longitudinal axes thereof are parallel to the surface of the base body.

2. A fine structure body as defined in claim 1 wherein a minor axis length of each of the metal nanorods falls within the range of 3 nm to 50 nm.

3. A fine structure body as defined in claim 1 wherein a major axis length of each of the metal nanorods falls within the range of 25 nm to 1,000 nm.

4. A fine structure body as defined in claim 2 wherein a major axis length of each of the metal nanorods falls within the range of 25 nm to 1,000 nm.

5. A fine structure body as defined in claim 1 wherein an aspect ratio of each of the metal nanorods, which aspect ratio is defined by a value of major axis length/minor axis length of each of the metal nanorods, falls within the range of more than 1 to 100, inclusive.

6. A fine structure body as defined in claim 2 wherein an aspect ratio of each of the metal nanorods, which aspect ratio is defined by a value of major axis length/minor axis length of each of the metal nanorods, falls within the range of more than 1 to 100, inclusive.

7. A fine structure body as defined in claim 3 wherein an aspect ratio of each of the metal nanorods, which aspect ratio is defined by a value of major axis length/minor axis length of each of the metal nanorods, falls within the range of more than 1 to 100, inclusive.

8. A fine structure body as defined in claim 4 wherein an aspect ratio of each of the metal nanorods, which aspect ratio is defined by a value of major axis length/minor axis length of each of the metal nanorods, falls within the range of more than 1 to 100, inclusive.

9. A fine structure body as defined in claim 1 wherein the fine structure body contains at least one region, in which at least one kind of spacing selected from the group consisting of the spacing between minor axis head regions of the metal nanorods adjacent to each other, the spacing between major axis side faces of the metal nanorods adjacent to each other, and the spacing between the minor axis head region of each of the metal nanorods and the major axis side face of the adjacent metal nanorod is equal to at most 10 nm.

10. A fine structure body as defined in claim 1 wherein the metal nanorods are constituted of a material containing at least one kind of substance selected from the group consisting of gold, silver, aluminum, and copper.

11. A Raman spectroscopic apparatus, comprising:
  a) a fine structure body comprising (i) a base body, and (ii) a plurality of metal nanorods, distributed and located on a surface of the base body, and each of which has a size capable of inducing localized surface plasmon resonance, the metal nanorods being provided such that the longitudinal axes thereof are parallel to the surface of the base body,
  b) light irradiating means for irradiating light to the surface of the fine structure body, on which surface the metal nanorods have been distributed and located, and
  c) spectroscopic means for separating scattered light of the light having been irradiated by the light irradiating means, which scattered light has been scattered from the surface of the fine structure body, into spectral components of the scattered light, and thereby obtaining a spectrum of the scattered light.

12. A Raman spectroscopic apparatus as defined in claim 11 wherein the fine structure body contains at least one region, in which at least one kind of spacing selected from the group consisting of the spacing between minor axis head regions of the metal nanorods adjacent to each other, the spacing between major axis side faces of the metal nanorods adjacent to each other, and the spacing between the minor axis head region of each of the metal nanorods and the major axis side face of the adjacent metal nanorod is equal to at most 10 nm.

* * * * *